US012667255B1

(12) United States Patent
Jiao et al.

(10) Patent No.: US 12,667,255 B1
(45) Date of Patent: Jun. 30, 2026

(54) MIXED REALITY (MR)-BASED OPTICAL DEVICE

(71) Applicants: Shuliang Jiao, Miami, FL (US); Rui Zhou, Miami, FL (US); Wei-Chiang Lin, Miami, FL (US)

(72) Inventors: Shuliang Jiao, Miami, FL (US); Rui Zhou, Miami, FL (US); Wei-Chiang Lin, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 19/381,742

(22) Filed: Nov. 6, 2025

(51) Int. Cl.
| | |
|---|---|
| *A61B 3/135* | (2006.01) |
| *A61B 3/00* | (2006.01) |
| *A61B 3/14* | (2006.01) |
| *G06F 3/14* | (2006.01) |
| *G06F 21/62* | (2013.01) |
| *G06T 7/00* | (2017.01) |
| *G06T 7/593* | (2017.01) |
| *G16H 40/67* | (2018.01) |
| *H04N 13/161* | (2018.01) |
| *H04N 13/189* | (2018.01) |
| *H04N 13/194* | (2018.01) |

(Continued)

(52) U.S. Cl.
CPC ........... *A61B 3/135* (2013.01); *A61B 3/0025* (2013.01); *A61B 3/0041* (2013.01); *A61B 3/14* (2013.01); *G06F 3/1454* (2013.01); *G06F 21/6245* (2013.01); *G06T 7/0012* (2013.01); *G06T 7/593* (2017.01); *G16H 40/67* (2018.01); *H04N 13/161* (2018.05); *H04N 13/189* (2018.05); *H04N 13/194* (2018.05);

*H04N 13/239* (2018.05); *H04N 13/246* (2018.05); *H04N 13/332* (2018.05); *G06T 2207/10021* (2013.01); *G06T 2207/30041* (2013.01)

(58) Field of Classification Search
CPC ..... A61B 3/135; A61B 3/0025; A61B 3/0041; A61B 3/14; G06F 3/1454; G06F 21/6245; G06T 7/0012; G06T 7/593; G06T 2207/10021; G06T 2207/30041; G16H 40/67; H04N 13/161; H04N 13/189; H04N 13/194; H04N 13/239; H04N 13/246; H04N 13/332
USPC ......................................................... 351/214
See application file for complete search history.

(56) References Cited

U.S. PATENT DOCUMENTS

| | | | | | |
|---|---|---|---|---|---|
| 5,993,001 | A | * | 11/1999 | Bursell | ................ H04N 13/341 348/E13.058 |
| 10,687,705 | B2 | * | 6/2020 | Dirghangi | .............. A61B 3/145 |

(Continued)

*Primary Examiner* — Mohammed A Hasan
(74) *Attorney, Agent, or Firm* — SALIWANCHIK, LLOYD & EISENSCHENK

(57) ABSTRACT

Systems and methods for generating a Mixed Reality (MR)-based optical device (e.g., MR-based slit lamp and/or MR-based microscope) are provided. The system utilizes two red, green, and blue (RGB) cameras of the MR device, substituting for operator's eyes to observe through the eyepieces of a slit lamp biomicroscope or a conventional optical microscope. The operator, wearing an MR headset, observes a three-dimensional (3D) visualization of examined eye region or, in the case of a microscope, the sample. The system enables slit lamp examinations to be conducted in a manner suitable for telemedicine, allowing multiple users to simultaneously view real-time images from the slit lamp and/or a microscope.

18 Claims, 10 Drawing Sheets

(51) Int. Cl.
    *H04N 13/239*     (2018.01)
    *H04N 13/246*     (2018.01)
    *H04N 13/332*     (2018.01)

(56)            References Cited

U.S. PATENT DOCUMENTS

| | | | |
|---|---|---|---|
| 2023/0396941 A1* | 12/2023 | Sturgeon | H04R 25/507 |
| 2024/0029881 A1* | 1/2024 | Singh | G16H 50/30 |
| 2024/0284085 A1* | 8/2024 | Vastare | H04M 1/724097 |
| 2025/0331708 A1* | 10/2025 | Edrei | A61B 3/0008 |

* cited by examiner

MIXED REALITY (MR)-BASED OPTICAL DEVICE

BACKGROUND

Slit lamp biomicroscopy is a fundamental diagnostic modality in ophthalmology, enabling detailed examination of both anterior and posterior ocular segments. Traditionally, slit lamps are designed to provide stereoscopic visualization, allowing clinicians to perceive depth and subtle anatomical variations. Conventional digital slit lamp system, which incorporate a camera or imaging sensor, offer advantages such as image capture, video recording, electronic storage, and remote sharing, beneficial for telemedicine, documentation, and education. However, most existing digital systems utilize a single-channel design, resulting in the loss of stereoscopic depth information and, consequently, a diminished capacity for depth perception. This limitation may impact both diagnostic accuracy and the effectiveness of clinical training.

BRIEF SUMMARY

To address the loss of depth perception in digital slit lamp systems, stereoscopic imaging techniques have been investigated. Employing real-time stereoscopic three-dimensional (3D) streaming for slit lamps has significant potential for enhancing visualization of spatial relationships within ocular tissues, thereby improving educational utility and clinical decision-making. Mixed Reality (MR) technology provides new opportunities for advanced 3D medical visualization. MR enables overlaying of digital content onto the physical environment, allowing users to interact with virtual elements in a spatially coherent and intuitive manner. This fusion of physical and digital environments presents unique advantages for healthcare applications, with ophthalmology identified as a key domain for its implementation.

Existing stereoscopic 3D visualization systems in ophthalmic microsurgery, including heads-up display systems, head-mounted displays, 3D camera-display systems, and endoscopic visualization systems have been employed to improve ergonomics, depth perception, and teaching value, while maintaining comparable clinical outcomes. However, challenges associated with seamless workflow integration, ergonomic accessibility for surgical assistants, overall system cost, and interoperability with existing slit lamp or microscope hardware remain significant barriers to widespread clinical adoption. To address the challenges, embodiments of the subject invention provide novel and advantageous systems and methods for generating an MR-based optical device (e.g., an MR-based slit lamp and/or an MR-based microscope).

In an embodiment, a system for generating an MR-based optical device (e.g., an MR-based slit lamp and/or an MR-based microscope) can comprise: a) a plurality of hardware modules integrated with a first optical device (e.g., a slit lamp and/or a microscope) and configured to capture real-time stereoscopic data through an optical path, the real-time stereoscopic data comprising both image data and video data, captured via the first optical device; b) a plurality of (local and/or remote) MR display devices operatively coupled to the plurality of hardware modules and configured to render the real-time stereoscopic data in an immersive environment; and c) a plurality of software modules configured to acquire, process, and transmit the real-time stereoscopic data to the plurality of (local and/or remote) MR display devices. The plurality of hardware modules can comprise: mounting hardware structurally connected to the first optical device configured to support integration of cameras across multiple models of the first optical device; and/or communication hardware configured to enable bidirectional data exchange with the plurality of (local and/or remote) MR display devices, thereby establishing a flexible platform interoperable with existing clinical optical device systems (e.g., clinical slit lamp systems and/or clinical microscope systems). The mounting hardware can comprise: a structure configured to facilitate efficient attachment to and detachment from the slit lamp and/or the microscope; a locking component configured to secure and maintain mechanical stability; and/or fine adjustment assemblies configured to align the cameras with respect to image centering, focal distance, and rotational orientation. The mounting hardware can be configured to: be compatible with both portable handheld and table-mounted models; achieve optimal alignment between optical axes of eyepieces of the first optical device and the cameras; and/or eliminate artifacts including vignetting, distortion, or partial image loss. The cameras can comprise a dual-channel video camera setup including two red, green, and blue (RGB) cameras configured to capture and stream the real-time stereoscopic data synchronously for immersive viewing, each camera being mounted onto the first optical device, and each camera being configured to preserve image resolution and depth perception consistent with the inherent optical characteristics of the first optical device. The communication hardware can comprise: integrated microphones and speakers within the plurality of (local and/or remote) MR display devices, configured to facilitate direct audio communication without the use of external devices; and/or communication components configured to optimize real-time data exchange by maintaining a streaming latency of less than 0.1 seconds between the (local and/or remote) MR display devices, a local computing device, and a remote streaming server. The plurality of software modules can comprise: i) a local application configured to support clinically intuitive interaction between a local operator and a patient, concurrently producing an enhanced, geometrically accurate three-dimensional (3D) visualization of an ocular region under examination; ii) a streaming application configured to allow transmission of the real-time stereoscopic data to remote physicians equipped with MR, augmented reality (AR), or virtual reality (VR) headsets, thereby enabling collaborative clinical examinations across distributed locations; and/or iii) a remote application configured to interface with one or more of the (local and/or remote) MR display devices, thereby enabling reliable data acquisition and interactive functionality, and the plurality of software modules further configured to record and store the real-time stereoscopic data for on-demand review, thereby enhancing telemedicine capabilities in ophthalmology and improving emergency response in ophthalmic clinics. The local application can comprise: a stream client configured to handle acquisition, encoding, and display of the real-time stereoscopic data; a head-mounted display (HMD) application configured to deliver an immersive real-time 3D video experience; and/or a camera calibration tool set configured to perform 3D calibration for accurate depth recovery, the camera calibration tool set being executable either in free space or with the camera mounted on the first optical device, thereby providing operational flexibility across various clinical configurations. The stream client can comprise: a camera interface configured to acquire the real-time stereoscopic data; a video encoder configured to compress the acquired real-time stereoscopic data; and/or a real-time communication protocol client configured to efficiently handle the real-time stereoscopic data from acquisition through transmission or storage. The HMD application can comprise: a 3D video player configured to receive the real-time stereoscopic data via a real-time streaming interface and to support playback of recorded videos with privacy controls including unique user authentication, data encryption, and audit logging protocols, the 3D video player configured to provide video enhancement features including adjustments for color, brightness, and contrast, as well as frame capture and digital magnification capabilities; and/or a diagnosis auxiliary toolkit configured to utilize two-dimensional (2D) image data and 3D stereoscopic data representing anatomical features of the ocular region to assist in diagnosis, the diagnosis auxiliary toolkit comprising a depth measurement module and an artificial intelligence (AI)-assisted module for ocular abnormality detection. The streaming application can comprise: a real-time communication interface configured to minimize latency for real-time applications including remote diagnosis; a backup streaming protocol configured to provide fallback streaming capability with broader compatibility; and/or a secure media transport protocol configured to encrypt the real-time stereoscopic data to ensure a high standard of data security for the protection of Protected Health Information (PHI), thereby facilitating compliance with Health Insurance Portability and Accountability Act (HIPAA).

In another embodiment, a method for generating an MR-based optical device (e.g., an MR-based slit lamp and/or an MR-based microscope) can comprise: a) a plurality of hardware modules integrated with a first optical device (e.g., a slit lamp and/or a microscope) and configured to capture real-time stereoscopic data through an optical path, the real-time stereoscopic data comprising both image data and video data, captured via the first optical device; b) a plurality of (local and/or remote) MR display devices operatively coupled to the plurality of hardware modules and configured to render the real-time stereoscopic data in an immersive environment; and c) a plurality of software modules configured to acquire, process, and transmit the real-time stereoscopic data to the plurality of (local and/or remote) MR display devices. The plurality of hardware modules can comprise: mounting hardware structurally connected to the first optical device configured to support integration of cameras across multiple models of the first optical device; and/or communication hardware configured to enable bidirectional data exchange with the plurality of (local and/or remote) MR display devices, thereby establishing a flexible platform interoperable with existing clinical optical device systems (e.g., slit lamp systems and/or microscope systems). The mounting hardware can comprise: a structure configured to facilitate efficient attachment to and detachment from the first optical device; a locking component configured to secure and maintain mechanical stability; and/or fine adjustment assemblies configured to align the cameras with respect to image centering, focal distance, and rotational orientation. The mounting hardware can be configured to: be compatible with both portable handheld and table-mounted models; achieve optimal alignment between optical axes of eyepieces of the first optical device and the cameras; and/or eliminate artifacts including vignetting, distortion, or partial image loss. The cameras can comprise a dual-channel video camera setup including two RGB cameras configured to capture and stream the real-time stereoscopic data synchronously for immersive viewing, each camera being mounted onto the first optical device, and each camera being configured to preserve image resolution and depth perception consistent with the inherent optical characteristics of the first optical device. The communication hardware can comprise: integrated microphones and speakers within the plurality of (local and/or remote) MR display devices, configured to facilitate direct audio communication without the use of external devices; and/or communication components configured to optimize real-time data exchange by maintaining a streaming latency of less than 0.1 seconds between the (local and/or remote) MR display devices, a local computing device, and a remote streaming server. The plurality of software modules can comprise: i) a local application configured to support clinically intuitive interaction between a local operator and a patient, concurrently producing an enhanced, geometrically accurate 3D visualization of an ocular region under examination; ii) a streaming application configured to allow transmission of the real-time stereoscopic data to remote physicians equipped with MR, AR, or VR headsets, thereby enabling collaborative clinical examinations across distributed locations; and/or iii) a remote application configured to interface with one or more of the (local and/or remote) MR display devices, thereby enabling reliable data acquisition and interactive functionality, and the plurality of software modules further configured to record and store the real-time stereoscopic data for on-demand review, thereby enhancing telemedicine capabilities in ophthalmology and improving emergency response in ophthalmic clinics. The local application can comprise: a stream client configured to handle acquisition, encoding, and display of the real-time stereoscopic data; an HMD application configured to deliver an immersive real-time 3D video experience; and/or a camera calibration tool set configured to perform 3D calibration for accurate depth recovery, the camera calibration tool set being executable either in free space or with the camera mounted on the first optical device, thereby providing operational flexibility across various clinical configurations. The stream client can comprise: a camera interface configured to acquire the real-time stereoscopic data; a video encoder configured to compress the acquired real-time stereoscopic data; and/or a real-time communication protocol client configured to efficiently handle the real-time stereoscopic data from acquisition through transmission or storage and the HMD application can comprise: a 3D video player configured to receive the real-time stereoscopic data via a real-time streaming interface and to support playback of recorded videos with privacy controls including unique user authentication, data encryption, and audit logging protocols, the 3D video player configured to provide video enhancement features including adjustments for color, brightness, and contrast, as well as frame capture and digital magnification capabilities; and/or a diagnosis auxiliary toolkit configured to utilize 2D image data and 3D stereoscopic data representing anatomical features of the ocular region to assist in diagnosis, the diagnosis auxiliary toolkit comprising a depth measurement module and an AI-assisted module for ocular abnormality detection. The streaming application can comprise: a real-time communication interface configured to minimize latency for real-time applications including remote diagnosis; a backup streaming protocol configured to provide fallback streaming capability with broader compatibility; and/or a secure media transport protocol configured to encrypt the real-time stereoscopic data to ensure a high standard of data security for the protection of PHI, thereby facilitating compliance with HIPAA.

BRIEF DESCRIPTION OF DRAWINGS

FIG. 2A shows an image of the standardized resolution test target captured using the camera at its maximum resolution setting of 4,656×3,496 pixels.

FIG. 2B shows a cropped region of interest (ROI) captured by the camera, highlighting additional details.

FIG. 2C shows an image of the standardized resolution test target captured from an MR headset during video streaming.

FIG. 2D shows a cropped ROI captured from the MR headset, highlighting additional details.

Scenario A (MR 2D 60 FPS): A non-stereoscopic two-dimensional (2D) video stream with an output resolution of 720p, where 'p' stands for progressive scan, at 60 frames per second (FPS) viewed through the MR headset;

Scenario B (MR 3D 30 FPS): A stereoscopic video stream with an output resolution of 720p at 30 FPS viewed through an MR headset;

Scenario C (MR 3D 60 FPS): A stereoscopic video stream with an output resolution of 720p at 60 FPS viewed through the MR headset; and Scenario D (Direct View): Direct optical observation through a conventional slit lamp, without the use of the MR headset.

Figure 4:
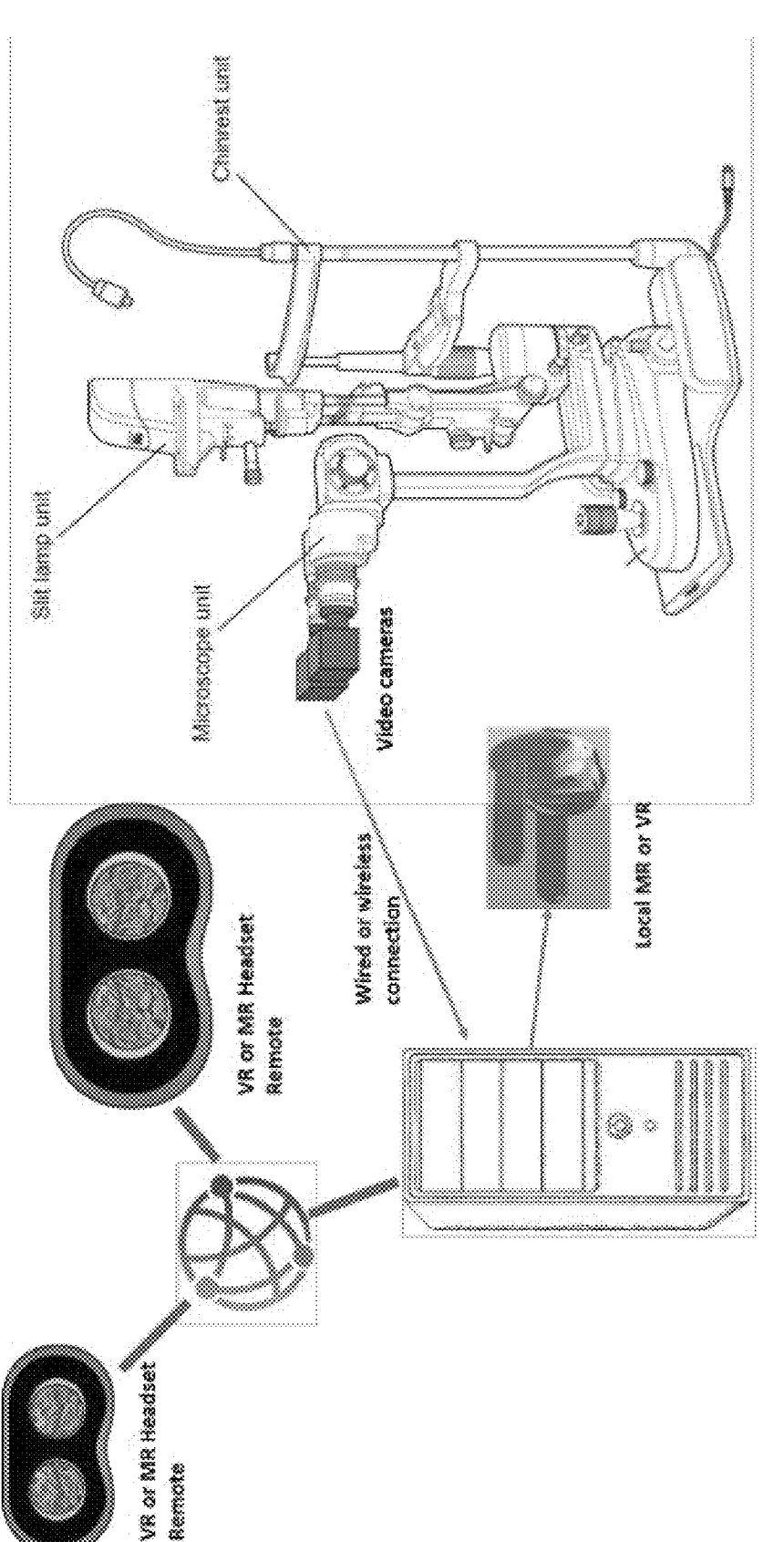

FIG. 4 shows high-resolution video cameras individually affixed to slit-lamp eyepieces using custom-designed adapters.

Figure 5:
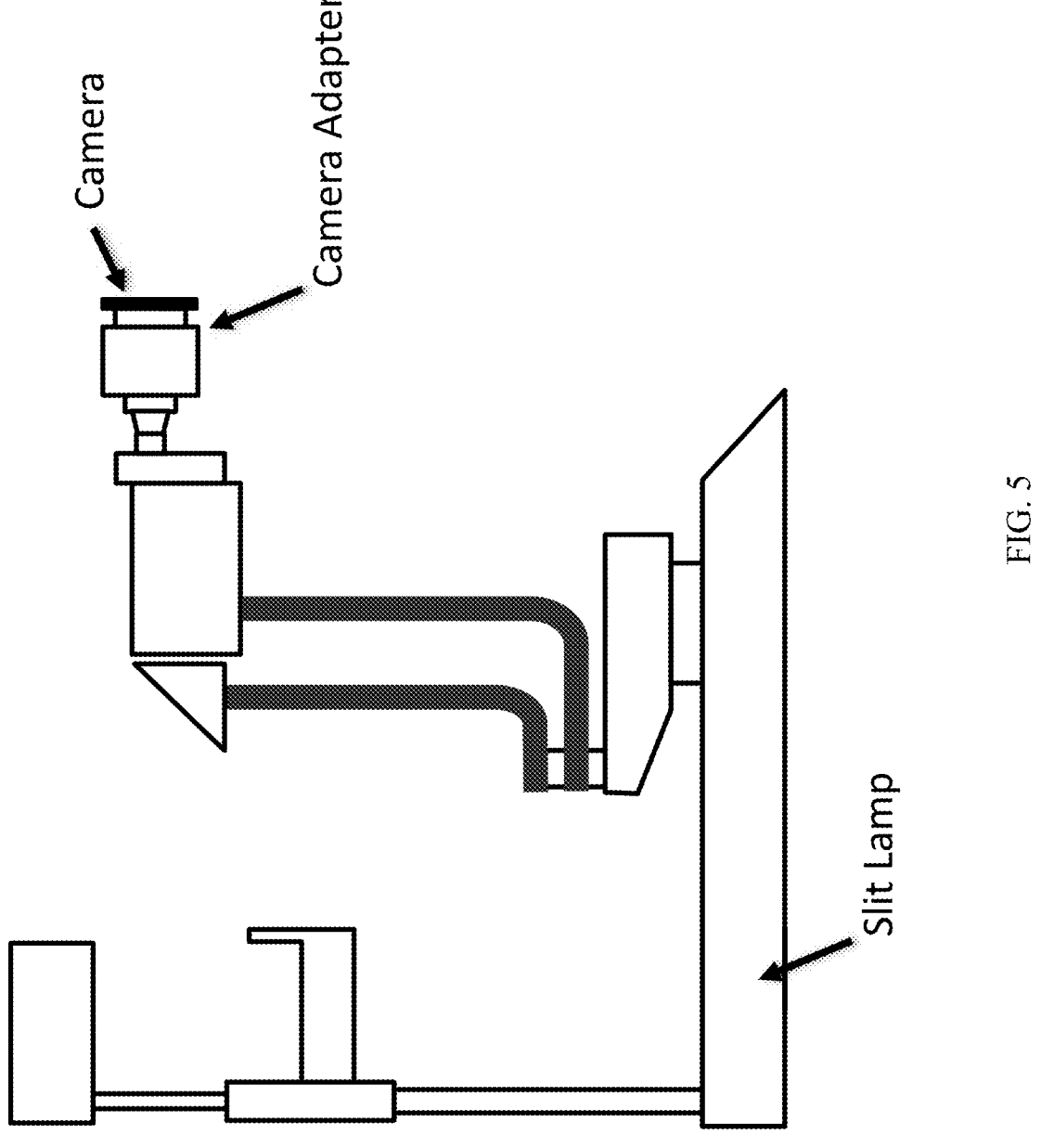

FIG. 5 shows a camera adapter configured to attach a camera to a slit lamp eyepiece.

Figure 6:
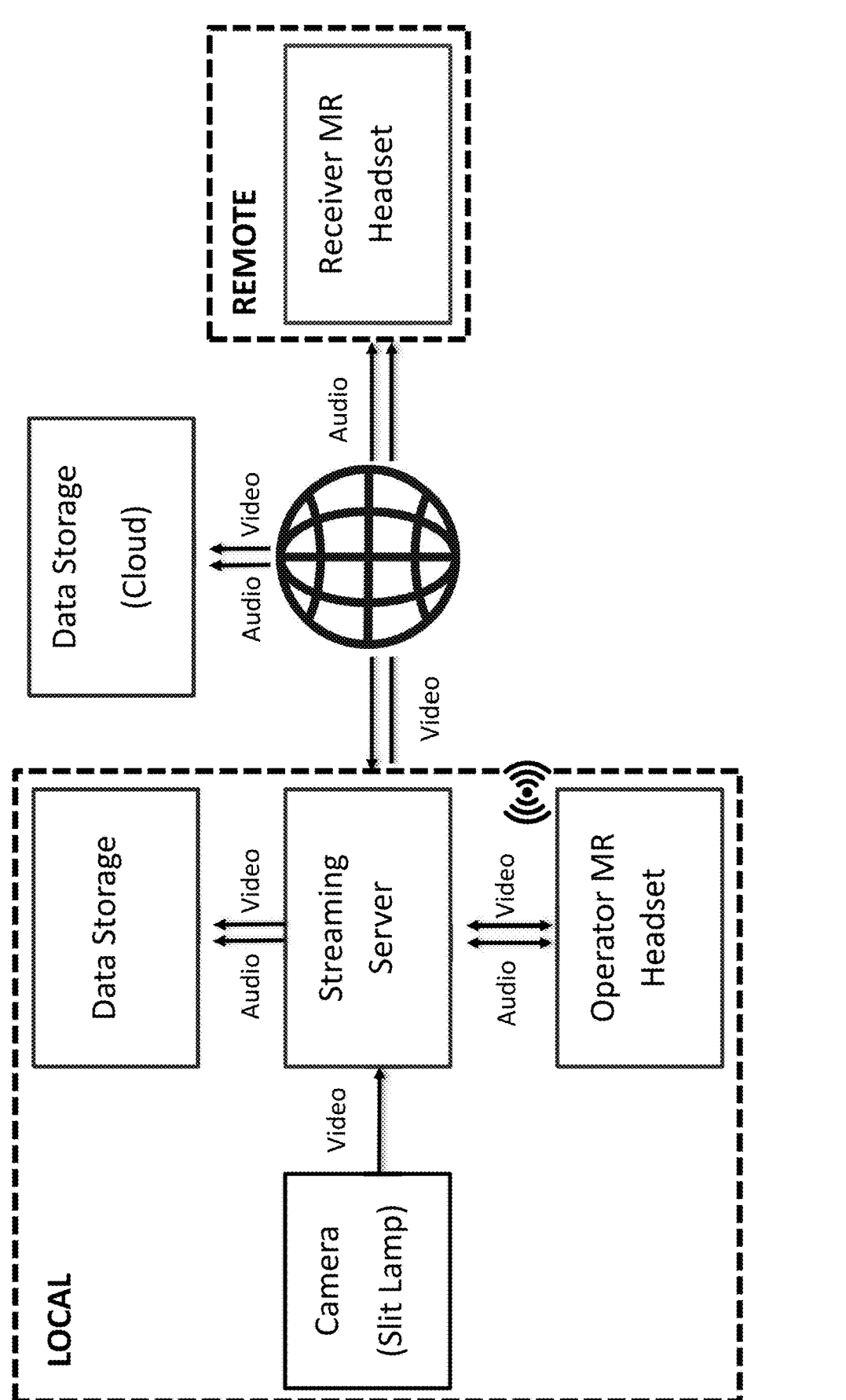

FIG. 6 shows a diagram of software and hardware architecture of MR-SLP, according to an embodiment of the subject invention.

Figure 7:
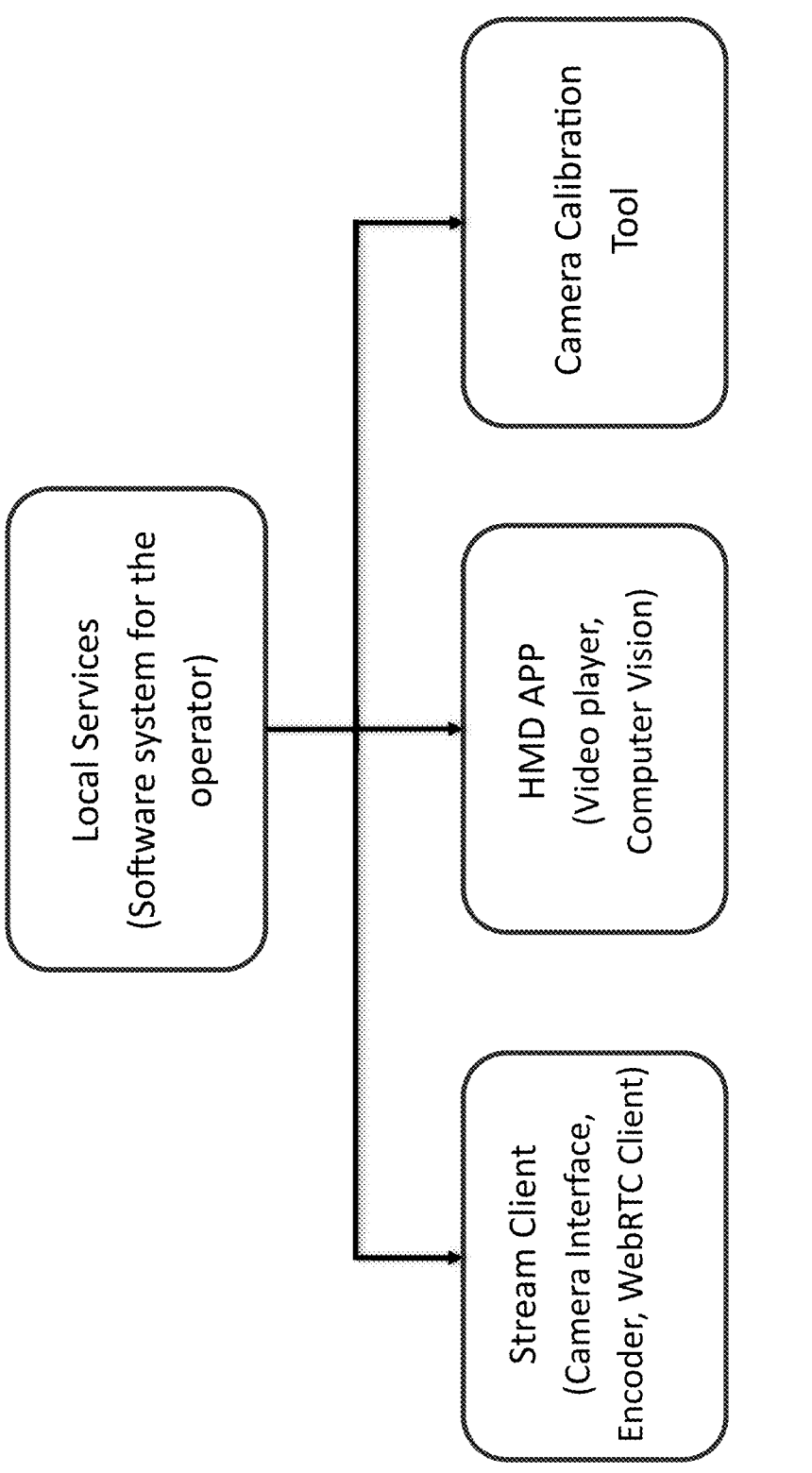

FIG. 7 shows a block diagram of functional components of a local application that operates locally within the system.

Figure 8:
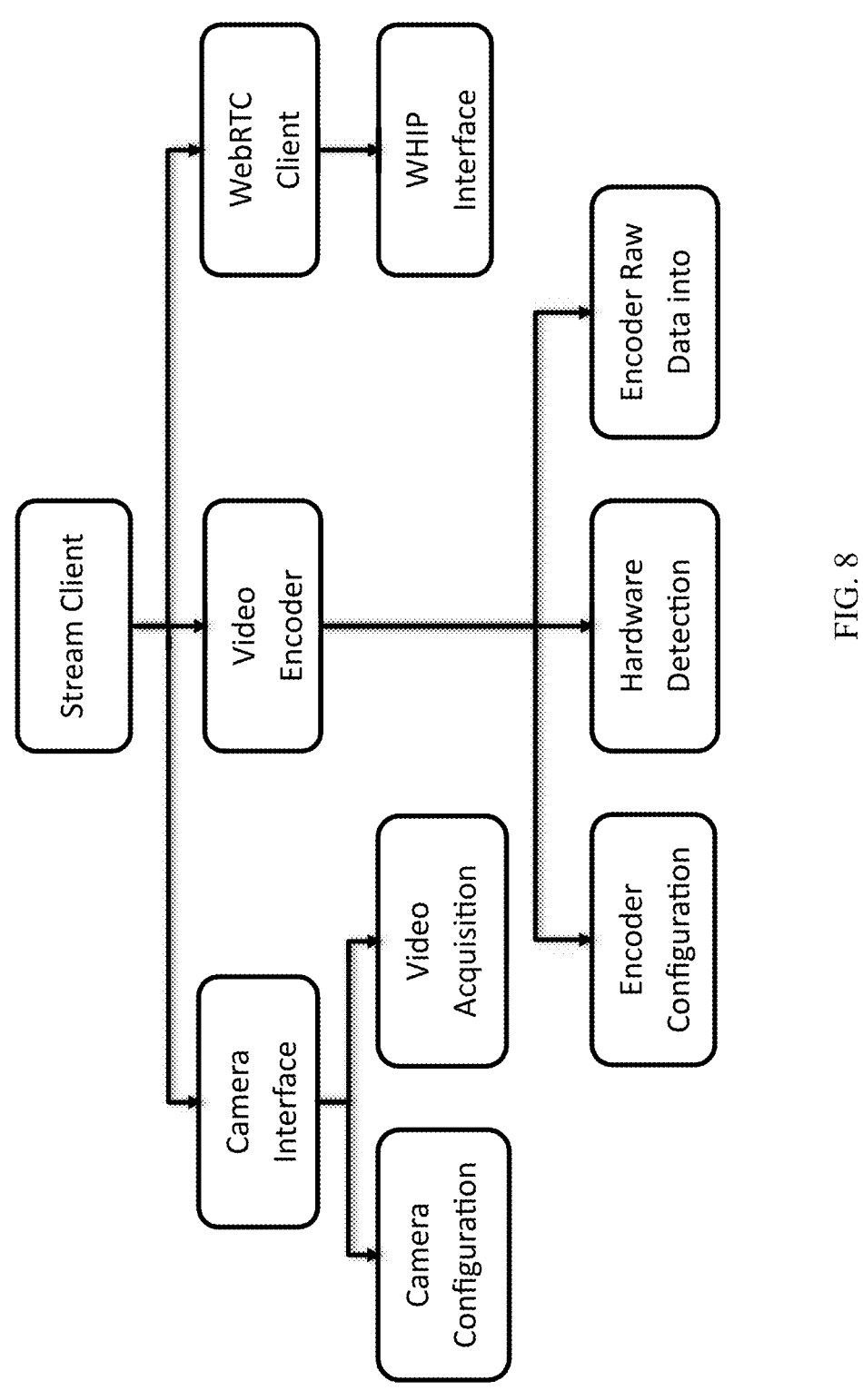

FIG. 8 shows a block diagram of functional components of a stream client, which forms part of the functional architecture of the local application. The stream client manages video data including acquisition, encoding, local display, and external casting to remote devices or displays.

Figure 9:
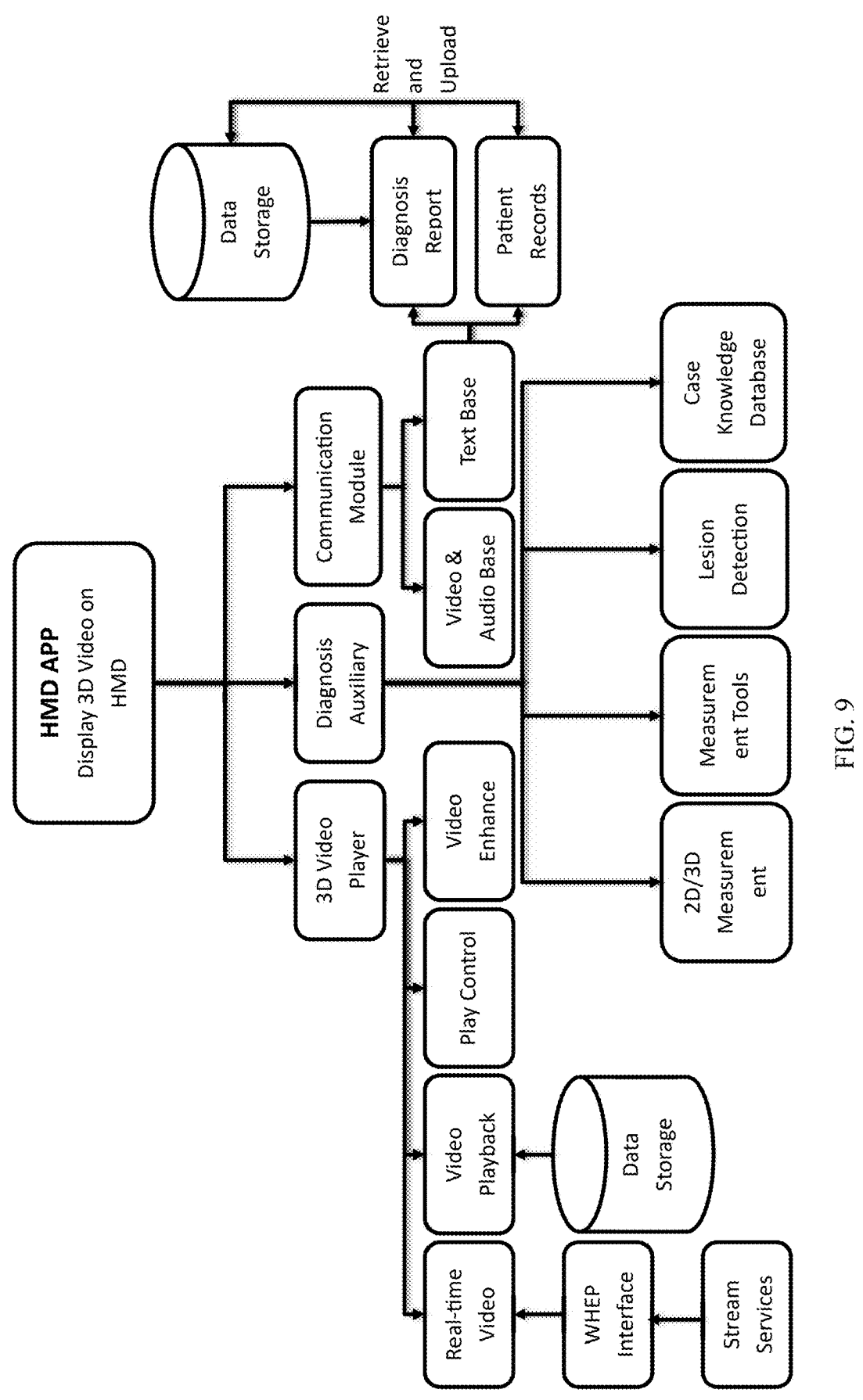

FIG. 9 shows a block diagram of functional components of a head-mounted display (HMD) application, also part of the local application's functional architecture. The HMD application is designed to deliver an immersive real-time 3D video experience.

DETAILED DESCRIPTION

Embodiments of the subject invention provide novel and advantageous systems and methods for generating a Mixed Reality (MR)-based slit lamp and/or MR-based microscope. A system, which can be referred to herein as a MR-based slit lamp (MR-SLP), combines MR technology with a slit lamp to enable real-time visualization and three-dimensional (3D) transmission of diagnostic images to multiple physicians through a communication network. The interactive capabilities enabled by MR, Virtual Reality (VR), and Augmented Reality (AR) technologies render MR-SLP suitable for both synchronous and asynchronous telemedicine applications. Unlike conventional slit lamp operation, MR-SLP allows the examiner to perform examinations without positioning their eyes near the eyepieces, while still achieving a stereoscopic view of the patient's eye. The disclosed system provides a novel approach to slit lamp operation, addressing limitations of conventional systems. Furthermore, current MR, VR, and AR technologies enable enhanced 3D visualization of the examined area through binocular vision.

The slit lamp is a stereoscopic biomicroscope that illuminates the eye using a focused beam of light with adjustable height, width, and angle. Utilizing binocular visualization with selectable magnifications, the slit lamp provides a 3D view of the anatomical structures of the eye. The slit lamp is a versatile and indispensable instrument in ophthalmological practice and is regarded as a standard device for examining the anterior segment of the eye, including the cornea, lens, and vitreous body. Additionally, the slit lamp is used to examine the iridocorneal angle and the posterior segment of the eye through contact and handheld lenses. Numerous procedures are performed under the slit lamp guidance, including foreign body removal, epilation of lashes, suture trimming, contact lens fitting, punctal plug insertion, and various minor surgical procedures. Furthermore, intraocular pressure (IOP) is measured using a Goldmann tonometer attached to the slit lamp.

Portable slit lamps have improved the accessibility of eye examinations by facilitating their use in remote settings. When combined with a camera, whether a dedicated or integrated within a smartphone, portable slit lamps serve as effective tools for teleophthalmology and tele-optometry. Currently, handheld slit lamps equipped with cameras capture two-dimensional (2D) images of the examination. However, such images fail to replicate the 3D depth perception available through the binocular eyepieces of conventional slit lamps. Consequently, off-site physicians do not experience the same level of immersion as during in-person examinations. Previous applications of AR and VR in slit lamps have predominantly focused on embedding digital information within the field of view, rather than providing true 3D viewing capabilities.

VR is an immersive technology that generates a simulated environment, which may replicate real-world scenarios or present entirely synthetic environments. AR overlays digital content, such as images, videos, or 3D objects, onto the physical environment, thereby enabling users to interact with both digital and physical elements simultaneously. MR integrates features of both AR and VR by merging digital content with the real-world environment, allowing interaction features between virtual and physical objects. The integration results in a user experience that is more interactive than conventional AR systems and more grounded in the physical environment than traditional VR systems. MR, VR, and AR technologies share several core components, including a head-mounted display (HMD), input devices, tracking systems, and computing hardware and software. An HMD is a wearable device to fit over the user's head and typically includes a dedicated display for each eye, along with sensors for tracking head and eye movements. The HMD delivers visual content to the user, generating a stereoscopic 3D view that enhances immersion. The performance and quality of the HMD significantly influence the user experience across MR, VR, and AR systems. As a result, substantial research and development efforts have been directed toward improving HMD technology. Recent advancements in display systems and optical components have further established MR as a promising platform for biomedical applications.

MR-SLP combines MR technology with the slit lamp to provide both local and remote examiners with access to 3D diagnostic images. The integration enables examiners to simultaneously view the patient and their surroundings using the passthrough functionality of MR systems. As a result, examination may be conducted more efficiently, while also allowing for more natural interaction with the patient. MR-SLP also addresses the discomfort associated with the close physical proximity typically required during conventional slit lamp examinations. The concern has become increasingly relevant in the context of the COVID-19 pandemic, where close face-to-face interaction between examiner and patient presents an elevated risk of disease transmission. Ophthalmologists are considered a high-risk group for such exposure. Accordingly, the ability of MR-SLP to facilitate slit lamp examinations at a safer distance enhances its practical value and relevance in clinical settings.

Embodiments of the subject invention integrate MR with the slit lamp to provide greater flexibility, enabling examiners to perform indirect eye examination and align the instrument appropriately without the need for close physical proximity. An AR or MR headset can assist on-site examiners during examination process. In addition, MR, VR, and AR technologies can be employed by remote examiners in telemedicine applications to facilitate real-time visualization, interaction, and collaborative assessment of medical data or patient conditions. The HMD can further be utilized to capture 3D images and videos for the purposes including diagnosis, follow-up assessments, and medical education.

Embodiments of the subject invention provide at least the following advantageous features. MR-SLP enables the examiner to obtain a 3D view of the eye without requiring direct viewing through the eyepiece, as is necessary in conventional slit lamp operation. The configuration affords the examiner greater freedom in operating the slit lamp and permits a safer working distance between the examiner and examinee, thereby reducing the risk of infectious disease transmission. The integration of MR technology simplifies 3D perception compared to traditional eyepieces-based viewing, where stereopsis can be easily disrupted by slight head movements. MR-SLP further enables the examiner to simultaneously view the patient and the surrounding environment, thereby supporting both stereoscopic visualization of the examined area and situational awareness during operation.

Additionally, MR-SLP facilitates advanced remote diagnostics and consultations in ophthalmic care by delivering a shared 3D stereoscopic view for local and remote users, enabling synchronous and asynchronous telemedicine. This real-time shared visual field enhances collaboration, communication, and diagnostic accuracy, transforming teleophthalmology from a 2D to a fully immersive 3D experience.

MR-SLP captures 3D images and videos at both local and remote locations, thereby enhancing education and training involving slit lamps. Trainees can engage in immersive simulations that replicate the experience of operating the slit lamp and viewing through the eyepieces in person. Additionally, multiple trainees can simultaneously observe real-time diagnostic images. MR-SLP provides comparable cost and communication requirements to those of smartphone-based slit lamps, while offering the advantage of 3D imaging rather than 2D imaging.

When employed in conjunction with a handheld slit lamp, the system delivers convenience and flexibility for portable and efficient eye examinations and screenings. The system obviates the need for 3D rendering to display diagnostic images with depth perception. Commercially available MR systems integrated into MR-SLP can be utilized without modification, provided the display resolution satisfies specified requirements. Internet communication protocols across various MR platforms are compatible, and applications for image acquisition, display, and sharing are developed on the Unity platform. The architecture facilitates straightforward adaptation to emerging MR systems and mitigates risks of product obsolescence. The implementation leverages fundamental MR and VR functionalities, which are less complex than those required in the gaming industry, thereby simplifying procurement of original equipment manufacturer (OEM) components.

MR-SLP introduces innovative features enhancing imaging, diagnostics, and user experience, including binocular image capture adaptable to various slit lamp models for stereoscopic imaging of anterior and posterior eye segments, quantitative measurements such as corneal thickness for improved diagnostic precision, and wavelength-dependent spectral illumination for functional imaging of ocular tissues. To support clinical performance and education, MR-SLP offers benefits such as superior depth perception and zoom capabilities, which help increase diagnostic accuracy and efficiency. Additionally, ergonomic design allows users to step back from the eyepieces, reducing neck and shoulder strain during extended use.

Hardware components are developed and integrated to enable MR capabilities on commercial slit lamps. The MR technology can be incorporated into standard and handheld portable slit lamps employed in ophthalmic clinical settings. Custom hardware components, including mounting systems, can be designed and fabricated to accommodate high-resolution cameras across various slit lamp models. Such development facilitates the creation of a versatile MR-SLP platform adaptable to existing slit lamps currently in use within clinical environments.

Any suitable MR headset, such as the Apple Vision Pro, may be utilized as the primary MR HMD for implementation of the system. In one embodiment, the Meta Quest 3 is employed for prototype development of the MR-SLP system due to its affordability and sufficient hardware specifications. Custom mounting hardware can be designed, fabricated and evaluated for integration with two types of slit lamp: (1) a portable handheld slit lamp, to assess applicability in mobile application, and (2) a conventional slit lamp mounted on an adjustable table, as shown in FIG. 5. The mounting hardware can be engineered to achieve optimal optical alignment between the slit lamp eyepieces and the associated cameras, thereby eliminating imaging artifacts such as vignetting, distortion, or partial image loss. Each mounting hardware can incorporate fine-tuning mechanisms to allow for image centering, adjustment of projection distance (focal length), and rotational alignment of the camera. Additionally, the mounting hardware can include a locking mechanism to ensure mechanical stability during standard slit lamp operation as well as a user-friendly interface to facilitate raped attachment and detachment. To ensure high quality, immersive 3D visualization of ocular structures, a software utility as camera calibration tool set can be employed during the camera and mounting hardware installation process.

Headset's passthrough color cameras can be utilized to directly capture images and videos through the slit lamp eyepieces. The cameras provide a resolution of approximately 4 million pixels (MP) with an angular resolution of 18 pixels per degree (PPD). The passthrough camera of the Meta Quest 3 offers a field of view (FOV) that is substantially wider than that of the slit lamp. As a result, the configuration does not optimally utilize the available resolution of the video cameras for slit lamp imaging applications. For the configuration utilizing independent cameras, as shown in FIG. 5, an array of video cameras can be evaluated based on several primary selection criteria. These criteria include sensor size, resolution (greater than or equal to 2K), frame rate (greater than or equal to 60 Hz), and bit depth (greater than or equal to 12 bits). Each candidate camera can be mounted onto the slit lamp for a series of performance evaluations. These evaluations can include verification of spatial resolution using a standardized resolution test target (US Air Force 1951 1X, Edmund Optics Inc., Barrington, NJ) and assessment of depth perception through the use of the Howard-Dolman Test or a comparable stereopsis test, conducted while viewing stereo images via Quest 3 HMD. Two video cameras, incorporating 1-inch and 2.8-inch 4K Sony Image Sensor (IMX298), can be optionally coupled to the eyepieces of a slit lamp. The specified FOV of these cameras is 75 degrees, which closely corresponds to the approximately 70-degree FOV of the slit lamp eyepiece as reported in the literature. At a magnification of 25×, the examiner can resolve Group 6, Element 5 of the standardized resolution test target when observing through the slit lamp eyepieces. As shown in FIGS. 2A-2D, images captured by the video cameras demonstrate comparable resolving capability, indicating that Group 6, Element 5 is likewise discernable. The discernability of Group 6, Element 5 in the captured images implies that MR-SLP can provide spatial resolution equivalent to that of direct visual observation through the eyepieces in local settings.

The configurations of MR-SLP, as shown in FIG. 5 involve stereo video cameras connected directly to a local computing device via a wired connection. The system, in conjunction with the associated software, can be evaluated to verify the audio and video transmission, specifically resolution, latency, and overall signal integrity, received by both the local computing system and the remote streaming server. For the implementation, the built-in audio communication system of the MR devices can be utilized to enable direct audio interaction, thereby eliminating the need for external communication hardware. Furthermore, the headset's passthrough cameras can be used to capture the examiner's actions during the procedure. The recorded video of the examiner's actions, while not needed for diagnostic, can be useful for educational and training applications.

Mounting hardware can be designed to provide mechanical stability and enable ergonomic, seamless integration with existing slit lamp models. Such mounting hardware can be fabricated and configured to facilitate compatibility with various configurations. The image resolution and depth perception achieved MR-SLP can be quantitatively assessed to establish equivalence to the native optical resolution and stereoscopic depth perception provided by direct observation through the slit lamp eyepieces. The communication hardware can be optimized to ensure consistent streaming performance, with latency maintained below 0.1 seconds between local MR devices, the local computing system, and the remove streaming server.

A comprehensive software platform for MR-SLP can be developed, comprising three functional modules: an operator MR application (local application), a streaming server application (streaming application), and a software application for remote MR and VR devices (remote application). FIG. 6 illustrates the software platform and its interaction with MR-SLP hardware components. These modules operate collaboratively to realize the full functionality or MR-SLP. The local application enables local operators to interact naturally with patients while providing an enhanced, undistorted 3D visualization of the examined ocular region. Concurrently, the streaming application facilitates the real-time transmission of 3D images and videos to remote physicians equipped with MR, AR, or VR headsets, thereby enabling collaborative remote examinations. The remote application supports seamless reception, visualization, and interaction with the streamed 3D content. Additionally, the software platform includes features for recording and on-demand review of 3D diagnostic videos and images, thereby, substantially improving telemedicine capabilities in ophthalmology and enhancing emergency response effectiveness in ophthalmic within clinical settings.

The local application enables operation by a local examiner and comprises three primary components, as shown in FIG. 7: a stream client, an HMD application, and a camera calibration tool set. The stream client, as shown in FIG. 8, serves as the central module for video data management, encompassing acquisition, encoding, displaying, and casting functions. The stream client includes three principal subcomponents: a Camera Interface to receive and process video input, one or more video encoders for compressing the video data, and a real-time communication protocol client for enabling real-time data transmission. This integrated architecture facilitates efficient processing of video data from initial capture through to transmission or storage. The HMD application, as shown in FIG. 9, provides an immersive 3D video experience in real time. The HMD application incorporates an advanced 3D video player, which receives streamed data via the real-time streaming interface and supports playback of recorded video content with integrated privacy protection mechanisms. The 3D video player includes video enhancement features, such as color adjustment, brightness and contrast controls, digital magnification, and frame capture functionality. In conjunction with the player, a diagnosis auxiliary toolkit can be developed to utilize both 2D and 3D data for diagnostic support, including tools for depth mapping and artificial intelligence (AI)-assisted detection of ocular abnormalities. The camera calibration tool set performs a critical function in recovering accurate depth information by enabling precise 3D camera calibration. This calibration can be conducted either in free space or with the camera mounted on a slit lamp, thereby offering flexibility. Collectively, the software components operate in an integrated manner to provide the examiner with a functional interface for conducting detailed ophthalmic examinations and supporting remote consultation and collaboration.

The streaming application utilizes advanced communication protocols to ensure high performance, low latency, and robust reliability for real-time image transmission. At its core, the system integrates a real-time communication interface configured to facilitate minimal-latency streaming, which is essential for time-sensitive applications such as remote diagnostic examinations. As a redundancy measure, a backup streaming protocol can be implemented to provide failover capability. Although the backup streaming protocol offers broad compatibility across platforms, the backup streaming protocol exhibits higher latency (exceeding approximately five seconds), making the backup streaming protocol suitable primarily as a contingency. To uphold stringent data security standards, a secure media transport protocol is employed to encrypt all streaming data transmissions, thereby ensuring secure and reliable communication between local and remote systems. The streaming software module additionally provides fine-grained control over multiple critical streaming parameters, including encoder selection, resolution, bitrate, and frame rate. The configurability enables the customization and optimization of transmission settings to accommodate specific operational constraints and clinical requirements.

Encoders: The system supports adaptable encoder selection compatible with diverse hardware environments. VP9 is designated as the recommended default encoder, providing an optimal balance between performance and hardware efficiency. Depending on the capabilities of the hardware, alternative encoders including H.264, H.265, and software-based encoders can be employed to achieve effective encoding.

Resolution: The effective video resolution displayed on the HMD is influenced by multiple factors, including the resolution of the imaging camera, the streaming configuration, the encoding capabilities, and the display specifications of the HMD. For instance, the Meta Quest 3 HMD includes a per-eye display resolution of 2064×2208 pixels, while the current 3D imaging camera is capable of capturing video at resolution up to 4656×3496 pixels. In consideration of performance constraints, hardware limitation, and network bandwidth efficiency, a default streaming resolution of 1920×1080 pixels (Full High Definition, FHD) has been selected to ensure reliable and high-quality transmission.

Bitrate: Bitrate denotes the data transmitted per unit time in a digital media stream, expressed in bits per second (bps), influencing transmission quality and bandwidth. Bitrate configurations are dynamically adjustable based on streaming architecture parameters, including encoder compression, output resolution, and frame rate. For video streaming at 1920×1080 pixels (FHD) at 30 frames per second (FPS), the system is configured to default to a bitrate of approximately 6 megabits per second (Mbps) for H.264 encoding, 4 Mbps for H.265, and 5 Mbps for VP9. In anticipation of HMD devices with support for Ultra High Definition (UHD, 2160p/4K) video output, the system is further designed to scale the bitrate dynamically to a range of approximately 15 to 25 Mbps, as required. These target bitrates are within the transmission capabilities of standard fourth-generation (4G) Long-Term Evolution (LTE) networks, which typically provide download speeds in the range of 15 to 20 Mbps and upload speeds between 10 to 15 Mbps. This ensures reliable and uninterrupted real-time streaming of FHD content under typical network conditions.

Frame Rate: The default frame rate is established at 30 FPS, corresponding to the capabilities of the current camera, which supports a maximum of 30 FPS at resolutions up to 2320×1744 pixels. Although higher frame rates reduce motion blur, higher frame rates substantially increase hardware and network demands, requiring optimized balance performance and resource utilization.

This comprehensive streaming solution ensures that MR-SLP can deliver high-quality, low-latency video streams while maintaining adaptability to diverse hardware configurations and network conditions.

The remote application shares the architectural framework of the local application. Functional permissions within the software are dynamically adjusted according to the user's role, thereby ensuring role-appropriate access and capabilities.

MR-SLP employs a comprehensive approach to protect Protected Health Information (PHI), ensuring compliance with Health Insurance Portability and Accountability Act (HIPAA) through robust physical, network, and procedural security measures. Physical safeguards include controlled to facilities, strict policies governing computer and electronic media use, and secure handling of electronic Protected Health Information (ePHI)-containing media. Technical safeguards encompass access controls utilizing unique user identifiers and encryption, detailed audit logging, and integrity verification mechanisms to prevent unauthorized alteration of ePHI. Additionally, the system incorporates Information Technology (IT) disaster recovery protocols and offsite backups to ensure data integrity and availability. Network and transmission security measures are implemented to protect ePHI during transfer across various communication channels, including email, internet, and private networks. This multi-layered security architecture meets and exceeds the requirements of HIPAA, thereby establishing a secure environment for managing sensitive patient information within MR-SLP. Through the deployment of comprehensive and rigorous security protocols, the system ensures the continuous confidentiality, integrity, and availability of critical health data.

The system development includes the implementation of a core streaming infrastructure, incorporating WebRTC, stream client and server components, and security protocols to ensure secure and reliable data transmission. An HMD application can be created and integrated, featuring a 3D video player, role-based access control, and full compatibility with the streaming infrastructure. The system can be validated and optimized through rigorous performance testing of key streaming parameters, including latency, resolution, and frame rate, along with comprehensive security audits and refinements to support efficient clinical deployment.

Embodiments of the subject invention provide a focused technical solution to the focused technical problem of how to generate MR-based slit lamps and/or MR-based microscopes. The solution is provided by integrating MR technology with a slit lamp and/or microscope, enabling real-time 3D imaging and video capture via a dual-channel camera system. Embodiments of the subject invention have the focused, technologically-specific practical application of enhanced telemedicine capabilities, improved medical education and training, augmented diagnostic accuracy, and streamlined clinical workflow. The generated MR-based slit lamp(s) and/or MR-based microscope(s) can be utilized (e.g., by personnel) during training, diagnosis (e.g., augmented diagnosis), and/or clinical work.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When the term module is used herein, it can refer to software and/or one or more algorithms to perform the function of the module; alternatively, the term module can refer to a physical device configured to perform the function of the module (e.g., by having software and/or one or more algorithms stored thereon).

When ranges are used herein, combinations and subcombinations of ranges (including any value or subrange contained therein) are intended to be explicitly included. When the term "about" or "approximately" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

Figure 1A:
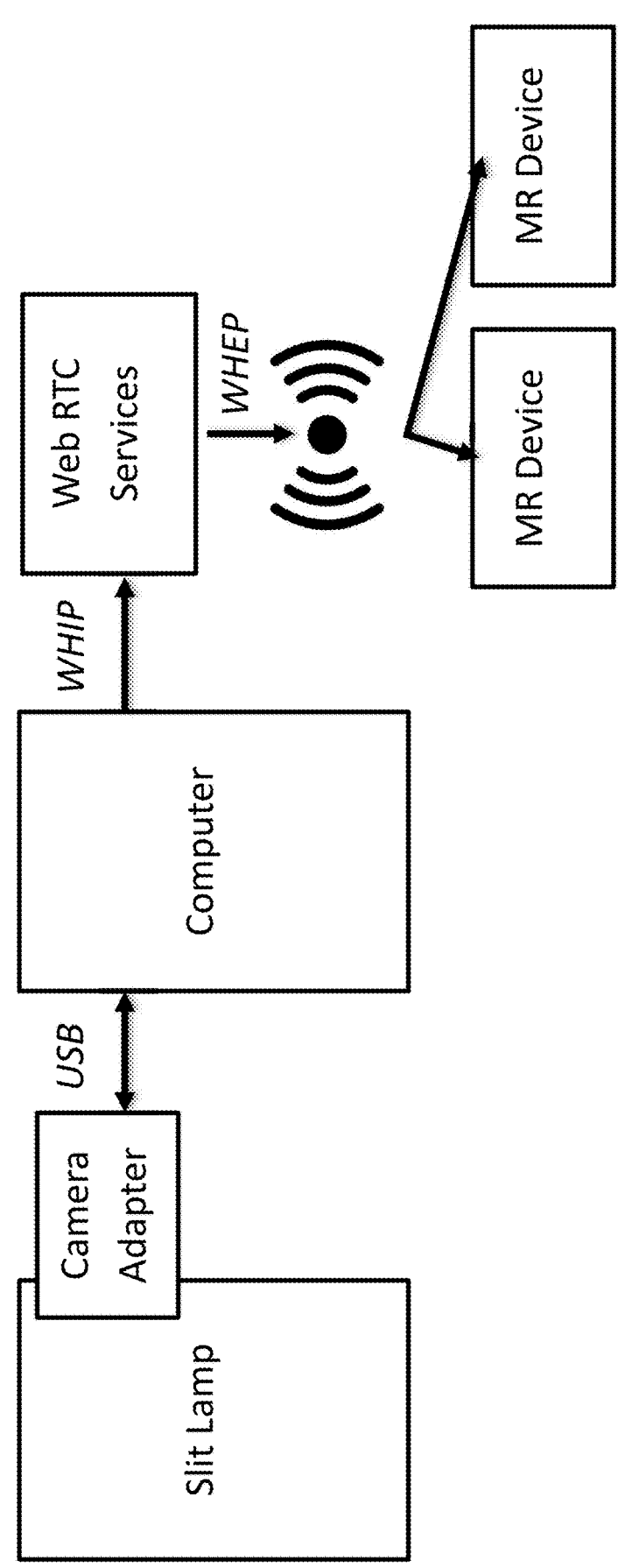
FIGS. 1A-1B show a schematic representation of a system, which can be referred to herein as a Mixed Reality-based slit lamp (MR-SLP), according to an embodiment of the subject invention, including a workflow diagram for data transmission (FIG. 1A) and a schematic representation of a three-dimensional (3D)-printed camera adapter for mounting cameras onto slit lamp (FIG. 1B).
Figure 1B:
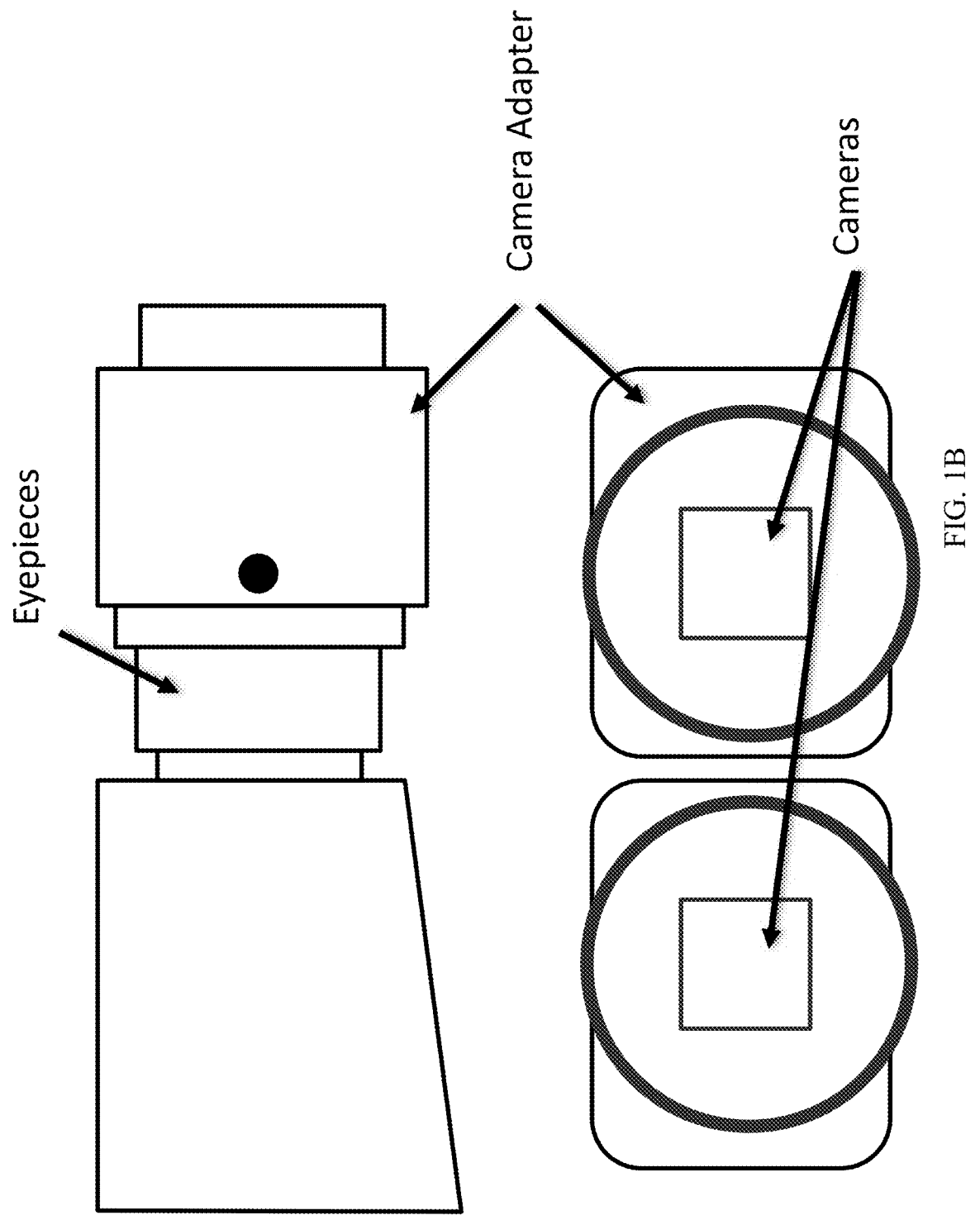
Figure 2A:
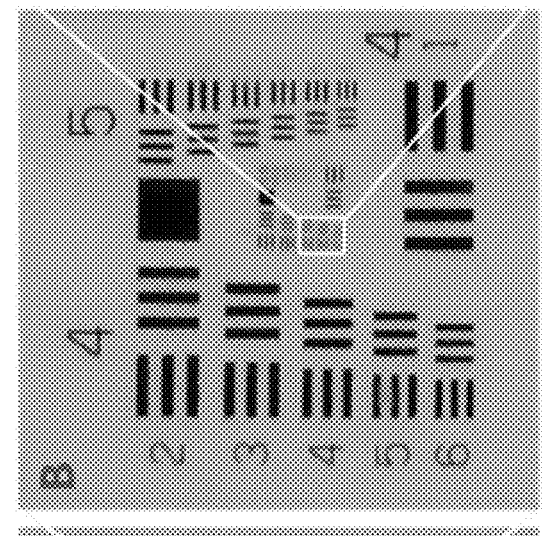
FIGS. 2A-2D collectively present spatial resolution measurements obtained from camera and MR headset, demonstrating system imaging performance through captured images of a standardized resolution test target (US Air Force 1951 1X, Edmund Optics Inc., Barrington, NJ) and corresponding analysis of minimum readable line pairs in horizontal and vertical orientations. The minimum readable line pairs appear substantially equivalent between the images. Intensity profiles were generated by calculating mean pixel intensity values across the line target regions, demonstrating distinct resolution of Group 6, Element 5 with clearly defined peaks and troughs corresponding to the line elements.
Figure 2B:
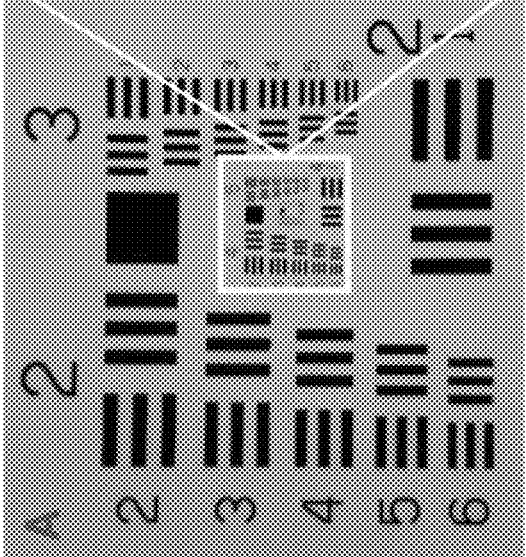
Figure 2C:
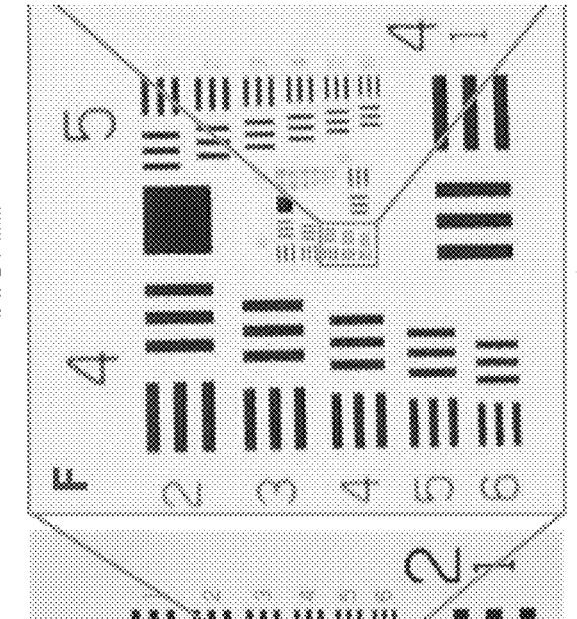
Figure 2D:
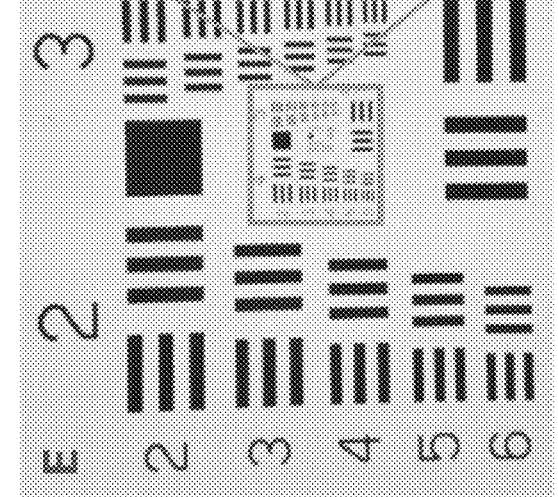

The hardware of the system comprises a commercial slit lamp (XCEL250, Recheit Inc, Depew, NY, USA, made in Italy) with built-in optical magnifications of 10×, 16× and 25×; a 3D video camera assembly; a local personal computer (PC) (DELL Precision 5820, Ubuntu Linux); and the MR headsets (Meta Quest 3 and Meta Quest Pro), as shown in FIG. 1A. Two USB cameras (ELP-USB16MP01-L75, 1/2.8-inch sensor, 16 million pixels, maximum resolution: 4656 (H)×3496 (V) pixels) were mounted on the slit lamp using a custom-designed 3D-printed mounting hardware, as shown in FIG. 1B. The mounting hardware ensured precise registration between the cameras and the eyepieces of the slit lamp. The adjustable Interpupillary Distance (IPD) was configurable via software and within the MR headsets.

Real-time videos from the cameras were captured and processed by Open Broadcaster Software (OBS) studio (64-bit, version 31.0), an open-source video streaming application, executed on a PC. The processing steps included: i) real-time video acquisition from each camera independently; ii) formatting of the videos from the two cameras into 3D side-by-side (SBS) mode; and iii) transmission of the formatted video to a WebRTC platform through WHIP employing H.264 encoding at a target bitrate approximately 10 Mbps and an output resolution of 1080p or 720p, where 'p' stands for progressive scan, indicating that each frame is displayed by drawing all lines sequentially. The numbers refer to the vertical pixel count. For local streaming tests, a free WebRTC platform, Open Source Simple Realtime Server (OSSRS)/Simple Realtime Server (SRS), available via Docker Hub was deployed on the PC, while a commercial WebRTC service provided by dolby.io was utilized for remote internet-based testing. The processed streams were transmitted wirelessly to the MR headsets using WHEP, as shown in FIG. 1A. A built-in Meta Quest video player rendered the SBS video into a stereoscopic view. Feedback was collected to assess perceptual differences among these views.

The spatial resolution was determined using the standardized resolution test target in conjunction with the slit lamp's built-in optical maximum magnification of 25×. The vertical and horizontal resolutions of the imaging camera and the MR display were measured independently. A subjective comparison was conducted in which participants evaluated and compared the image quality across three viewing modalities: direct optical observation through the slit lamp, the digital camera feed, and the MR-based visualization. To evaluate depth perception, a tube-threading task was devised. The tube-threading task comprised two sequential steps. First, participants were instructed to grasp each of ten tubes, having inner diameters ranging from 1 mm to 0.5 mm, using a high-precision tweezers designed for microscopy applications (Fisherbrand PL-30). Second, a 0.2 mm diameter wire was to be threaded into each of the tubes while operating under the slit lamp at 10× magnification. This tube-threading task was designed to assess the user's ability to perceive depth accurately and manipulate fine objects under magnified, stereo visualization conditions.

The tube-threading task was required to be performed continuously under four scenarios:

Scenario A (MR 2D 60 FPS): A non-stereoscopic 2D video stream with an output resolution of 720p, where 'p' stands for progressive scan, at 60 frames per second (FPS) viewed through the MR headset;

Scenario B (MR 3D 30 FPS): A stereoscopic video stream with an output resolution of 720p at 30 FPS viewed through an MR headset;

Scenario C (MR 3D 60 FPS): A stereoscopic video stream with an output resolution of 720p at 60 FPS viewed through the MR headset; and Scenario D (Direct View): Direct optical observation through a conventional slit lamp, without the use of the MR headset.

An ophthalmologist with more than 5 years of clinical experience volunteered to participate in the test. The participant exhibited normal vision acuity of 20/20 and demonstrated stereo vision with a minimum stereo-acuity of approximately 40 arcseconds, as assessed using random-dot stereogram (RDS) charts. The volunteer was instructed to repeat the tube-threading task ten times under each of the four scenarios. The time required to complete the tube-threading task in each scenario was recorded in order to evaluate operational efficiency.

A statistical analysis was conducted using analysis of variance (ANOVA), followed by a post hoc comparison with Bonferroni correction. P value of less than 0.05 was considered to indicate a statistically significant difference in time consumption between the evaluated scenarios.

Example 1

To validate the core concepts of MR-SLP, a Meta Quest 3 was utilized as the local MR HMD, while both Quest 3 and Quest Pro were employed as remote MR HMDs. The local MR HMD was integrated with a commercial slit lamp (XCEL 250, Reichert) for image acquisition and visualization. Two distinct configurations were evaluated in the preliminary studies. In the first configuration, the pass-through cameras of the HMD were used to acquire images through the eyepieces of the slit lamp. The MR HMD was securely affixed to the slit lamp using a custom mounting hardware, which ensured precise alignment of the headset's left and right cameras with the corresponding eyepieces of the slit lamp. Stereoscopic examination images were presented on the local HMD and simultaneously transmitted with remote MR HMDs via the internet. The second configuration, as shown in FIG. 4, employed two individual video cameras, each securely mounted on the left and right eyepieces using custom mounting hardware. The high-resolution images captured by these cameras were transmitted to a computer, which streamed the images in real time to both the local and remote HMDs via a high-speed internet connection, thereby ensuring synchronized visualization across all platforms.

At the local site, the first configuration required the operator to wear the headset while positioned at the slit lamp to view stereoscopic diagnostic images. The second configuration permitted the operator to wear the headset independently, eliminating the need for direct proximity to the eyepieces and face-to-face interaction with the imaging subject. Remote participants utilizing Quest 3 or Quest Pro headsets viewed real-time images identical to those seen by the slit lamp operator. Tests were conducted across two remote locations: the Engineering Campus of Florida International University, approximately one mile from the slit lamp, and a collaborator's residence about 20 miles from the slit lamp.

In the experiments, the stereoscopic eye images were displayed on an adjustable virtual plane, enabling users to optimize viewing distance. No discernible differences were observed in image quality, including resolution, color fidelity, and contrast, between the local and remote devices. Notably, both the local operator and the remote observer experienced identical 3D perception of the examined eye. The identical visual experience provided the remote participant with an immersive sensation akin to personally operating the slit lamp. The system also facilitated synchronized audio communication. This seamless integration of high-quality visual and auditory elements enabled smooth interaction between the local operator and the remote viewer. This smooth interaction fostered a synchronized and immersive experience, allowing both parties to work together as if co-located despite geographic separation.

A stereoscopic image pair of the human eye was captured at both local and remote sites. The environments at each site were recorded using respective MR devices. During the experiments, the stereoscopic eye images were rendered on an adjustable virtual plane, allowing users to optimize viewing distance according to individual preference. The images were representative frames extracted from video recordings obtained at the local and remote locations. Testing revealed no discernible differences in image quality, including resolution, color fidelity, and contrast, between the local and remote devices. Notably, both the local operator and the remote observer perceived the same 3D structure of the examined eye. The consistency in visual perception afforded the remote participant an immersive experience, comparable to personally operating the slit lamp. The system further supported synchronized audio communication, which, when combined with the high-quality visual stream, enabled fluid and uninterrupted interaction between the local operator and the remote viewer. This seamless integration of audiovisual elements facilitated a shared operational environment, thereby allowing both parties to engage collaboratively as though present in the same physical space, despite geographic separation.

Using the inherent optical magnification of 25× provided by the slit lamp, the spatial resolutions measured from both the camera and from the MR headset were observed to be nearly identical. The minimum readable line pairs corresponded to element 5 in group 6 of the standardized resolution test target, representing 102 line pairs (lp)/mm, with an approximate spacing of 9.8 μm between two adjacent lines, as shown in FIGS. 2A-2D. Three participants from FIU, each exhibiting normal visual acuity (20/20), reported that the minimum readable line pairs when viewing directly through the slit lamp ranged between Element 5 (102 lp/mm) and Element 6 (114 lp/mm). Additionally, the participants noted that the lines appeared marginally clearer during direct optical observation compared to those viewed through the MR headset.

Figure 3:
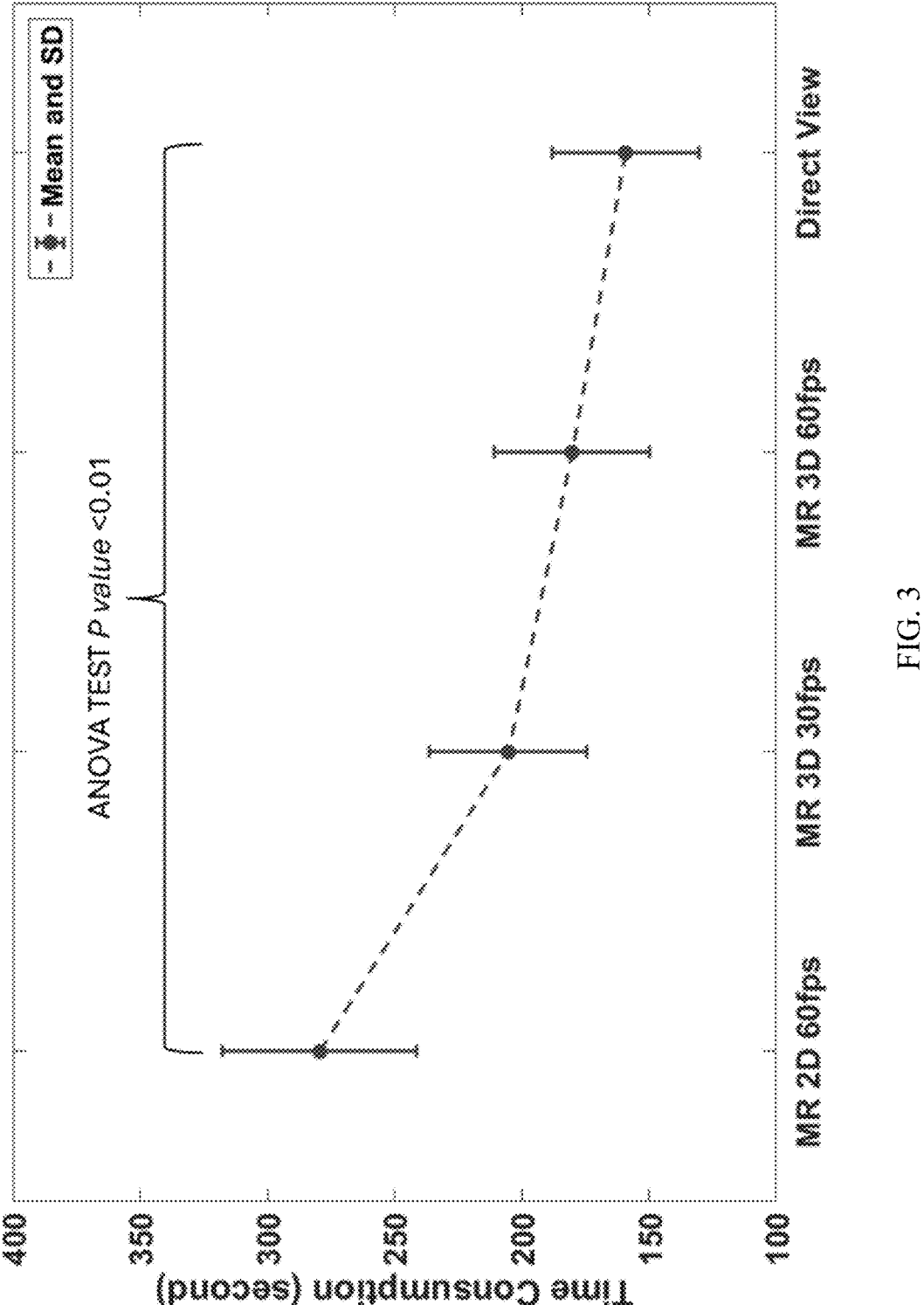
FIG. 3 shows time consumption associated with tube-threading task performance under four scenarios. Each data point represents the mean tube-threading task completion time (n=10), and the vertical bars indicate the standard deviation (SD) for each scenario. A statistically significant difference in time consumption was observed among the four scenarios (P<0.01), as determined by an Analysis of Variance (ANOVA). The tube-threading task was performed under the following four scenarios.

The average tube-threading task completion time was lowest under the direct viewing scenario, followed in order by MR 3D 60 FPS, MR 3D 30 FPS, and MR 2D 60 FPS scenarios, as shown in FIG. 3. The ANOVA test, followed by a post hoc test with Bonferroni correction was conducted to compare the time consumption across the four scenarios. The statistical analysis revealed no significant difference in tube-threading task completion time between the direct optional viewing through the slit lamp and the stereoscopic 3D mode at 60 FPS while wearing the MR headset with.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for generating a Mixed Reality (MR)-based optical device, the system comprising:

a) a plurality of hardware modules integrated with a first optical device and configured to capture real-time stereoscopic data through an optical path, the real-time stereoscopic data comprising both image data and video data, captured via the first optical device;

b) a plurality of MR display devices operatively coupled to the plurality of hardware modules and configured to render the real-time stereoscopic data in an immersive environment; and c) a plurality of software modules configured to acquire, process, and transmit the real-time stereoscopic data to the plurality of MR display devices, the first optical device comprising at least one of a slit lamp and a microscope, the MR-based optical device comprising at least one of an MR-based slit lamp and an MR-based microscope, the plurality of software modules comprising:

i) a local application configured to support clinically intuitive interaction between a local operator and a patient, concurrently producing an enhanced, geometrically accurate three-dimensional (3D) visualization of an ocular region under examination;

ii) a streaming application configured to allow transmission of the real-time stereoscopic data to remote physicians equipped with MR, augmented reality (AR), or virtual reality (VR) headsets, thereby enabling collaborative clinical examinations across distributed locations; and iii) a remote application configured to interface with one or more of the plurality of MR display devices, thereby enabling reliable data acquisition and interactive functionality, and the plurality of software modules further configured to record and store the real-time stereoscopic data for on-demand review, thereby enhancing telemedicine capabilities in ophthalmology and improving emergency response in ophthalmic clinics.

2. The system according to claim 1, the plurality of hardware modules comprising:

mounting hardware structurally connected to the first optical device configured to support integration of cameras across multiple models of the first optical device; and communication hardware configured to enable bidirectional data exchange with the plurality of MR display devices, thereby establishing a flexible platform interoperable with existing clinical optical device systems, the clinical optical device systems comprising at least one of a clinical slit lamp system and a clinical microscope system.

3. The system according to claim 2, the mounting hardware comprising:

a structure configured to facilitate efficient attachment to and detachment from the first optical device;

a locking component configured to secure and maintain mechanical stability; and fine adjustment assemblies configured to align the cameras with respect to image centering, focal distance, and rotational orientation, the mounting hardware configured to:

be compatible with both portable handheld and table-mounted models;

achieve optimal alignment between optical axes of eyepieces of the first optical device and the cameras; and eliminate artifacts including vignetting, distortion, or partial image loss.

4. The system according to claim 2, the cameras comprising a dual-channel video camera setup including two red, green, and blue (RGB) cameras configured to capture and stream the real-time stereoscopic data synchronously for immersive viewing, each camera being mounted onto the first optical device, and each camera being configured to preserve image resolution and depth perception consistent with the inherent optical characteristics of the first optical device.

5. The system according to claim 2, the communication hardware comprising:

integrated microphones and speakers within the plurality of MR display devices, configured to facilitate direct audio communication without the use of external devices; and communication components configured to optimize real-time data exchange by maintaining a streaming latency of less than 0.1 seconds between the plurality of MR display devices, a local computing device, and a remote streaming server.

6. The system according to claim 1, the local application comprising:

a stream client configured to handle acquisition, encoding, and display of the real-time stereoscopic data;

a head-mounted display (HMD) application configured to deliver an immersive real-time 3D video experience; and a camera calibration tool set configured to perform 3D calibration for accurate depth recovery, the camera calibration tool set being executable either in free space or with the camera mounted on the first optical device, thereby providing operational flexibility across various clinical configurations.

7. The system according to claim 6, the stream client comprising:

a camera interface configured to acquire the real-time stereoscopic data;

a video encoder configured to compress the acquired real-time stereoscopic data; and a real-time communication protocol client configured to efficiently handle the real-time stereoscopic data from acquisition through transmission or storage.

8. The system according to claim 6, the HM application comprising:

a 3D video player configured to receive the real-time stereoscopic data via a real-time streaming interface and to support playback of recorded videos with privacy controls including unique user authentication, data encryption, and audit logging protocols, the 3D video player configured to provide video enhancement features including adjustments for color, brightness, and contrast, as well as frame capture and digital magnification capabilities; and a diagnosis auxiliary toolkit configured to utilize two-dimensional (2D) image data and 3D stereoscopic data representing anatomical features of the ocular region to assist in diagnosis, the diagnosis auxiliary toolkit comprising a depth measurement module and an artificial intelligence (AI)-assisted module for ocular abnormality detection.

9. The system according to claim 1, the streaming application comprising:

a real-time communication interface configured to minimize latency for real-time applications including remote diagnosis;

a backup streaming protocol configured to provide fallback streaming capability with broader compatibility; and a secure media transport protocol configured to encrypt the real-time stereoscopic data to ensure a high standard of data security for the protection of Protected Health Information (PHI), thereby facilitating compliance with Health Insurance Portability and Accountability Act (HIPAA).

10. A method for generating a Mixed Reality (MR)-based optical device, the method comprising:

a) a plurality of hardware modules integrated with a first optical device and configured to capture real-time stereoscopic data through an optical path, the real-time stereoscopic data comprising both image data and video data, captured via the first optical device;

b) a plurality of MR display devices operatively coupled to the plurality of hardware modules and configured to render the real-time stereoscopic data in an immersive environment; and c) a plurality of software modules configured to acquire, process, and transmit the real-time stereoscopic data to the plurality of MR display devices, the first optical device comprising at least one of a slit lamp and a microscope, the MR-based optical device comprising at least one of an MR-based slit lamp and an MR-based microscope, the plurality of software modules comprising:

i) a local application configured to support clinically intuitive interaction between a local operator and a patient, concurrently producing an enhanced, geometrically accurate three-dimensional (3D) visualization of an ocular region under examination;

ii) a streaming application configured to allow transmission of the real-time stereoscopic data to remote physicians equipped with MR, augmented reality (AR), or virtual reality (VR) headsets, thereby enabling collaborative clinical examinations across distributed locations; and iii) a remote application configured to interface with one or more of the plurality of MR display devices, thereby enabling reliable data acquisition and interactive functionality, and the plurality of software modules further configured to record and store the real-time stereoscopic data for on-demand review, thereby enhancing telemedicine capabilities in ophthalmology and improving emergency response in ophthalmic clinics.

11. The method according to claim 10, the plurality of hardware modules comprising:

mounting hardware structurally connected to the first optical device configured to support integration of cameras across multiple models of the first optical device; and communication hardware configured to enable bidirectional data exchange with the plurality of MR display devices, thereby establishing a flexible platform interoperable with existing clinical optical device systems, the clinical optical device systems comprising at least one of a clinical slit lamp system and a clinical microscope system.

12. The method according to claim 11, the mounting hardware comprising:

a structure configured to facilitate efficient attachment to and detachment from the first optical device;

a locking component configured to secure and maintain mechanical stability; and fine adjustment assemblies configured to align the cameras with respect to image centering, focal distance, and rotational orientation, the mounting hardware configured to:

be compatible with both portable handheld and table-mounted models;

achieve optimal alignment between optical axes of eyepieces of the first optical device and the cameras; and eliminate artifacts including vignetting, distortion, or partial image loss.

13. The method according to claim 11, the cameras comprising a dual-channel video camera setup including two red, green, and blue (RGB) cameras configured to capture and stream the real-time stereoscopic data synchronously for immersive viewing, each camera being mounted onto the first optical device, and each camera being configured to preserve image resolution and depth perception consistent with the inherent optical characteristics of the first optical device.

14. The method according to claim 11, the communication hardware comprising:

integrated microphones and speakers within the plurality of MR display devices, configured to facilitate direct audio communication without the use of external devices; and communication components configured to optimize real-time data exchange by maintaining a streaming latency of less than 0.1 seconds between the plurality of MR display devices, a local computing device, and a remote streaming server.

15. The method according to claim 10, the local application comprising:

a stream client configured to handle acquisition, encoding, and display of the real-time stereoscopic data;

a head-mounted display (HMD) application configured to deliver an immersive real-time 3D video experience; and a camera calibration tool set configured to perform 3D calibration for accurate depth recovery, the camera calibration tool set being executable either in free space or with the camera mounted on the first optical device, thereby providing operational flexibility across various clinical configurations.

16. The method according to claim 15, the stream client comprising:

a camera interface configured to acquire the real-time stereoscopic data;

a video encoder configured to compress the acquired real-time stereoscopic data; and a real-time communication protocol client configured to efficiently handle the real-time stereoscopic data from acquisition through transmission or storage, and the HMD application comprising:

a 3D video player configured to receive the real-time stereoscopic data via a real-time streaming interface and to support playback of recorded videos with privacy controls including unique user authentication, data encryption, and audit logging protocols, the 3D video player configured to provide video enhancement features including adjustments for color, brightness, and contrast, as well as frame capture and digital magnification capabilities; and a diagnosis auxiliary toolkit configured to utilize two-dimensional (2D) image data and 3D stereoscopic data representing anatomical features of the ocular region to assist in diagnosis, the diagnosis auxiliary toolkit comprising a depth measurement module and an artificial intelligence (AI)-assisted module for ocular abnormality detection.

17. The method according to claim 10, the streaming application comprising:

a real-time communication interface configured to minimize latency for real-time applications including remote diagnosis;

a backup streaming protocol configured to provide fallback streaming capability with broader compatibility; and a secure media transport protocol configured to encrypt the real-time stereoscopic data to ensure a high standard of data security for the protection of Protected Health Information (PHI), thereby facilitating compliance with Health Insurance Portability and Accountability Act (HIPAA).

18. A system for generating a Mixed Reality (MR)-based optical device, the system comprising:

a) a plurality of hardware modules integrated with a first optical device and configured to capture real-time stereoscopic data through an optical path, the real-time stereoscopic data comprising both image data and video data, captured via the first optical device;

b) a plurality of MR display devices operatively coupled to the plurality of hardware modules and configured to render the real-time stereoscopic data in an immersive environment; and c) a plurality of software modules configured to acquire, process, and transmit the real-time stereoscopic data to the plurality of local MR display devices, the plurality of hardware modules comprising:

mounting hardware structurally connected to the first optical device configured to support integration of cameras across multiple models of the first optical device; and communication hardware configured to enable bidirectional data exchange with the plurality of MR display devices, thereby establishing a flexible platform interoperable with existing clinical optical device systems, the mounting hardware comprising:

a structure configured to facilitate efficient attachment to and detachment from the first optical device;

a locking component configured to secure and maintain mechanical stability; and fine adjustment assemblies configured to align the cameras with respect to image centering, focal distance, and rotational orientation, the mounting hardware configured to:

be compatible with both portable handheld and table-mounted models;

achieve optimal alignment between optical axes of eyepieces of the first optical device and the cameras; and eliminate artifacts including vignetting, distortion, or partial image loss, the cameras comprising a dual-channel video camera setup including two red, green, and blue (RGB) cameras configured to capture and stream the real-time stereoscopic data synchronously for immersive viewing, each camera being mounted onto the first optical device, and each camera being configured to preserve image resolution and depth perception consistent with the inherent optical characteristics of the first optical device, the communication hardware comprising:

integrated microphones and speakers within the plurality of MR display devices, configured to facilitate direct audio communication without the use of external devices; and communication components configured to optimize real-time data exchange by maintaining a streaming latency of less than 0.1 seconds between the plurality of MR display devices, a local computing device, and a remote streaming server, the plurality of software modules comprising:

i) a local application configured to support clinically intuitive interaction between a local operator and a patient, concurrently producing an enhanced, geometrically accurate three-dimensional (3D) visualization of an ocular region under examination;

ii) a streaming application configured to allow transmission of the real-time stereoscopic data to remote physicians equipped with MR, augmented reality (AR), or virtual reality (VR) headsets, thereby enabling collaborative clinical examinations across distributed locations; and iii) a remote application configured to interface with one or more of the plurality of MR display devices, thereby enabling reliable data acquisition and interactive functionality, the plurality of software modules further configured to record and store the real-time stereoscopic data for on-demand review, thereby enhancing telemedicine capabilities in ophthalmology and improving emergency response in ophthalmic clinics, the local application comprising:

a stream client configured to handle acquisition, encoding, and display of the real-time stereoscopic data;

a head-mounted display (HMD) application configured to deliver an immersive real-time 3D video experience; and a camera calibration tool set configured to perform 3D calibration for accurate depth recovery, the camera calibration tool set being executable either in free space or with the camera mounted on the first optical device, thereby providing operational flexibility across various clinical configurations, the stream client comprising:

a camera interface configured to acquire the real-time stereoscopic data;

a video encoder configured to compress the acquired real-time stereoscopic data; and a real-time communication protocol client configured to efficiently handle the real-time stereoscopic data from acquisition through transmission or storage, the HMD application comprising:

a 3D video player configured to receive the real-time stereoscopic data via a real-time streaming interface and to support playback of recorded videos with privacy controls including unique user authentication, data encryption, and audit logging protocols;

the 3D video player configured to provide video enhancement features including adjustments for color, brightness, and contrast, as well as frame capture and digital magnification capabilities; and a diagnosis auxiliary toolkit configured to utilize two-dimensional (2D) image data and 3D stereoscopic data representing anatomical features of the ocular region to assist in diagnosis, the diagnosis auxiliary toolkit comprising a depth measurement module and an artificial intelligence (AI)-assisted module for ocular abnormality detection, the streaming application comprising:

a real-time communication interface configured to minimize latency for real-time applications including remote diagnosis;

a backup streaming protocol configured to provide fallback streaming capability with broader compatibility; and a secure media transport protocol configured to encrypt the real-time stereoscopic data to ensure a high standard of data security for the protection of Protected Health Information (PHI), thereby facilitating compliance with Health Insurance Portability and Accountability Act (HIPAA), the first optical device comprising at least one of a slit lamp and a microscope, the MR-based optical device comprising at least one of an MR-based slit lamp and an MR-based microscope, and the clinical optical device systems comprising at least one of a clinical slit lamp system and a clinical microscope system.

\* \* \* \* \*